(12) United States Patent
Damikolas

(10) Patent No.: US 6,213,343 B1
(45) Date of Patent: Apr. 10, 2001

(54) PORTABLE STERILE BANDAGE DISPENSER

(75) Inventor: Gerry Damikolas, Upland, CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 09/170,478

(22) Filed: Oct. 13, 1998

(51) Int. Cl.[7] .................................................. B65D 85/67
(52) U.S. Cl. ................................. 221/25; 225/10; 221/73
(58) Field of Search ................................ 221/25, 71, 72, 221/73, 74; 225/10, 11, 12, 13, 14, 15, 16

(56) References Cited

U.S. PATENT DOCUMENTS

| | | |
|---|---|---|
| 3,530,494 | 9/1970 | Baratta . |
| 3,955,711 * | 5/1976 | Schroter et al. ...................... 221/73 |
| 4,560,087 * | 12/1985 | Sato et al. .............................. 221/73 |
| 4,576,311 * | 3/1986 | Horton et al. .......................... 221/73 |
| 4,664,306 * | 5/1987 | Levy ....................................... 227/67 |
| 4,735,342 * | 4/1988 | Goldstein ............................... 221/25 |
| 4,993,586 | 2/1991 | Taulbee et al. . |
| 5,005,730 * | 4/1991 | Pickrell, Jr. et al. .................. 221/71 |
| 5,065,894 | 11/1991 | Garland . |
| 5,213,653 * | 5/1995 | Akahori et al. ....................... 156/584 |
| 5,234,093 * | 8/1993 | Abe et al. .............................. 194/296 |
| 5,358,140 | 10/1994 | Pellegrino . |
| 5,482,182 * | 1/1996 | Thompson et al. .................... 221/73 |
| 5,806,713 * | 9/1998 | Dudley et al. ......................... 221/73 |
| 5,863,384 * | 1/1999 | Reddy .................................. 156/576 |
| 5,906,701 * | 5/1999 | Smythe ................................ 156/249 |

* cited by examiner

Primary Examiner—Christopher P. Ellis
Assistant Examiner—Rashmi Sharma
(74) Attorney, Agent, or Firm—Oppenheimer Wolff & Donnelly LLP

(57) ABSTRACT

A novel bandage dispenser is disclosed for dispensing bandages from a roll of sterilized, individually wrapped bandages. Several bandage feeding mechanisms are disclosed, to serially dispense a bandage and simultaneously strip off the liner surrounding the bandage, upon depression of a hand actuated switch. Also disclosed is an improved roll of bandages suitable for use in the bandage dispenser.

18 Claims, 5 Drawing Sheets

PORTABLE STERILE BANDAGE DISPENSER

BACKGROUND OF THE INVENTION

1. Field of Invention

The present invention relates generally to dispensers for sealed bandages.

2. Description of Related Art

Various dispensers for bandages have been proposed in the art. To date, however, none of the prior art dispensers teach, show or suggest the present novel design.

For example, U.S. Pat. No. 5,065,894 to Garland discloses a dispenser for bandages that strips the outer wrapping of the bandage; however, inter alia, Garland discloses a bulky, wall-mounted design that does not lend itself to manufacture into an easily portable, hand-held unit as the present design, nor does the complicated gearing in Garland suggest the compact design of the present invention.

U.S. Pat. No. 3,530,494 to Baratta, U.S. Pat. No. 5,358,140 to Pellegrino and U.S. Pat. No. 4,993,586 to Taulbee et al., are examples of rolls of bandages dispensed by manually pulling the bandages from a roll; however, neither of these references suggest the present invention, as they lack, inter alia, a way of dispensing a bandage mechanically.

SUMMARY OF THE INVENTION

The present invention is an improved bandage dispenser that allows bandages to be dispensed serially from a roll. The bandage dispenser dispenses bandages one at a time whenever an actuator is depressed.

One aspect of one embodiment of the invention involves the dispensing of bandages ready for immediate application to the injured area, without the need to separately remove the covering liners from the bandage.

Another aspect of one embodiment of the present invention is to provide for a bandage dispenser that can dispense an integral multiple of individual bandages, with the bandages sealed in a wrapper lining, for later use.

Still another aspect of one embodiment of the present invention is to provide for a bandage roll having an improved design for use in a dispenser as disclosed herein.

Yet another aspect of one embodiment of the present invention is to provide an improved drive mechanism for engaging the bandage roll of the dispenser and dispensing bandages while simultaneously stripping off the bandage liners. To this end, several improved drive mechanisms are disclosed. In one preferred embodiment a rack and pinion drives a plurality of cooperating pinch rollers.

Another aspect of one embodiment of the present invention is to provide a dispenser with a modern, compact design that can be mass-produced, be lightweight, portable and readily fit in a user's hand.

In accordance with a specific illustrative embodiment of the invention , a handheld bandage dispenser includes a roll of bandages, with each bandage being individually wrapped, the bandages serially connected together at their longitudinal ends, with the top and bottom liners surrounding the sterile bandages having pressure sensitive adhesive securing the liners together. The dispenser includes a pair of pinch rollers and a finger actuated drive mechanism for rotating the pinch rollers to dispense one or more bandages.

The above described and many other features and attendant advantages of the present invention will become apparent by reference to the following detailed description when considered in conjunction with the accompanying drawings.

BRIEF DESCRIPTION OF THE DRAWINGS

A detailed description of preferred embodiments of the invention will be made with reference to the accompanying drawings.

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention. The section titles and overall organization of the present detailed description are for the purpose of convenience only and are not intended to limit the present invention.

Figure 1:
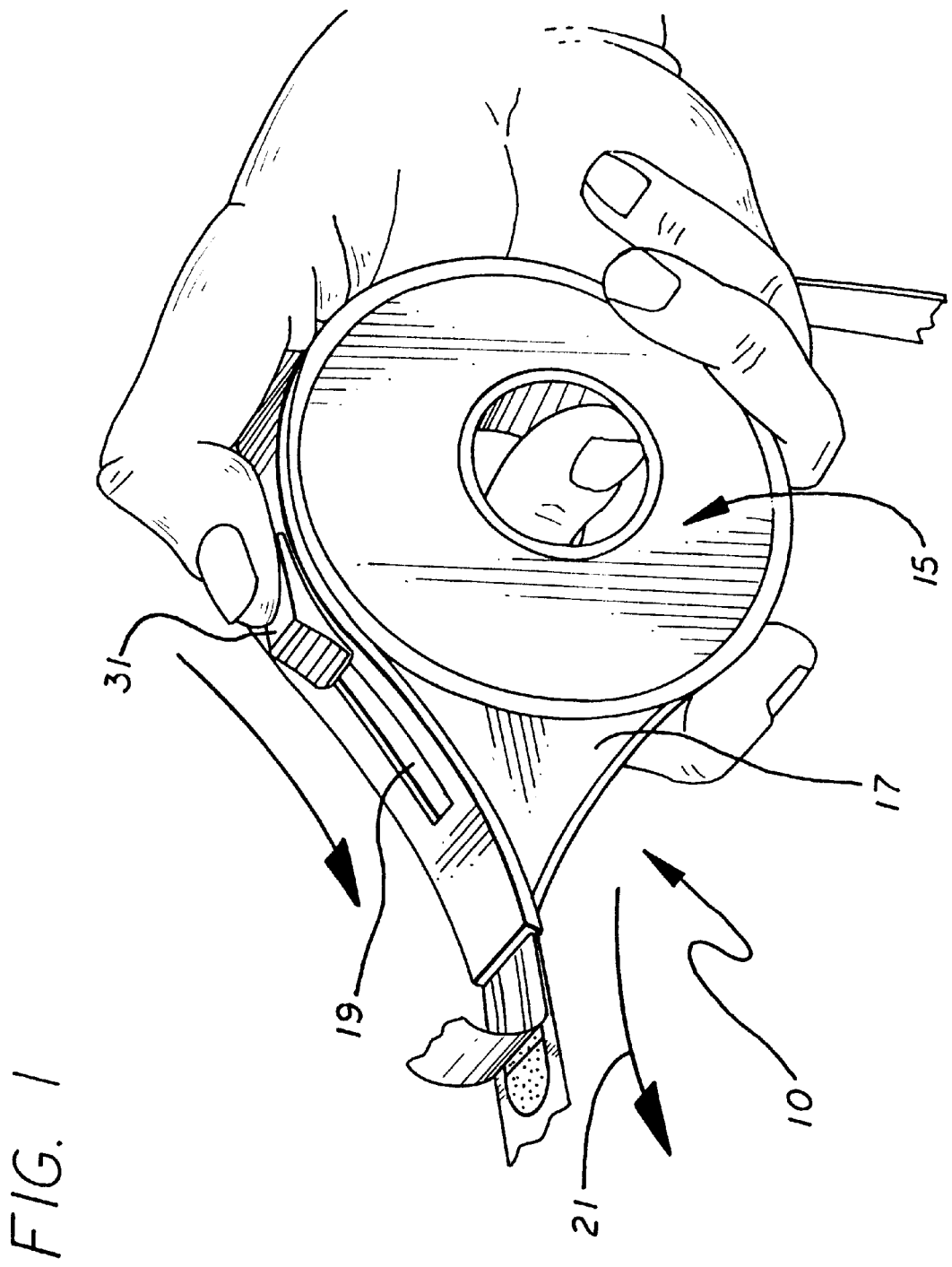
FIG. 1 is a perspective view of the dispenser, showing a user operating the dispenser.

FIG. 1 discloses a plan view of the dispenser 10, having a dispenser assembly 17 including a housing enclosing a roll 15 of sealed, serially-connected, sterile bandages. The bandage roll 15, which may be wrapped about a reel or simply rolled into a roll on a disposable core or mandrel, can be replaceable and removable from the dispenser 10, or affixed permanently and sealed therein, as for single use only. Individual bandages (e.g., Band-Aids®, a registered trademark of Johnson & Johnson, One Johnson & Johnson Plaza, New Brunswick, N.J., 08933-7003), as known per se, are dispensed from the dispenser 10 ready to be applied. The bandages have an adhesive portion bisected by a gauze pad, and are sandwiched between a top and bottom liner, with the sticky surfaces on one side exposed. As shown, the outside frame of dispenser 10 fits easily in an adult hand, and forms a hand handle, being less than 12 inches in linear dimension in any one direction, and of a portable, lightweight construction, which may be plastic.

Figure 2:
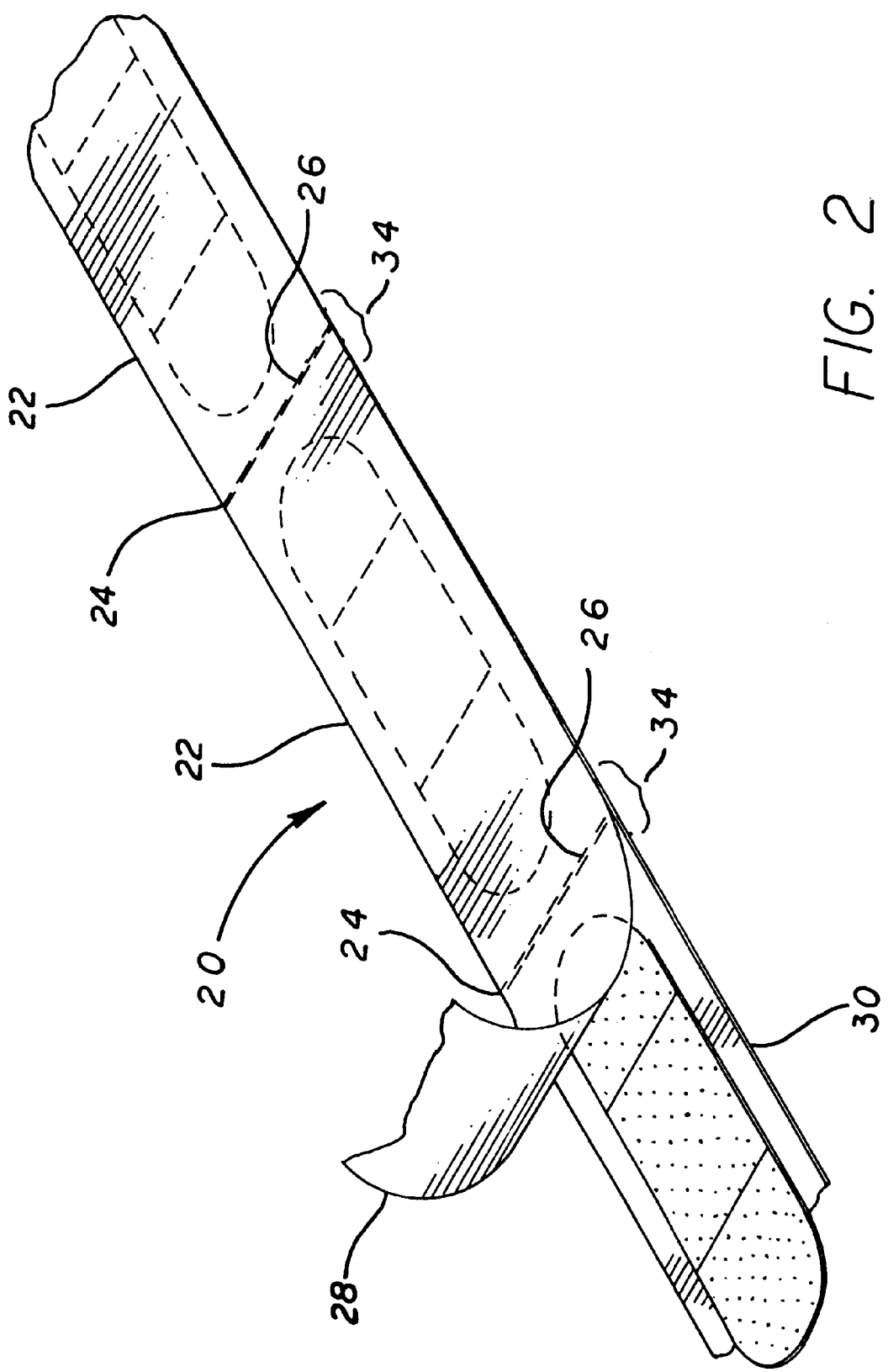
FIG. 2 is a view of the bandages from the bandage roll used in the dispenser of the present invention.
Figure 3:
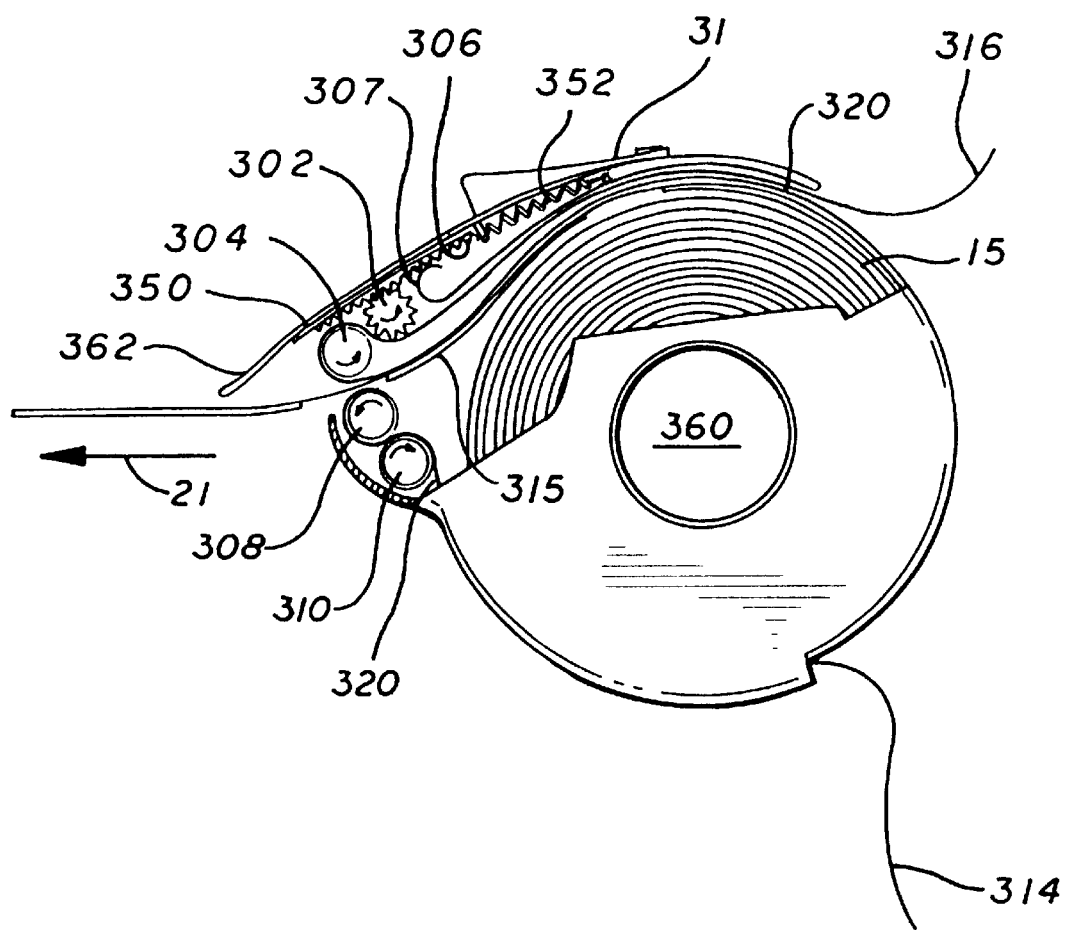
FIG. 3 is a cut away radial cross-sectional view of the dispenser, holding a roll of sterile sealed bandages.

Referring to FIGS. 2 and 3, bandages 20 are supplied wrapped as a roll 15. The roll 15 is formed of a plurality of individual bandages 22 attached together serially at their ends 24. The bandages are scored with separation perforations 26 at ends 24. Each bandage 22 is lined with an upper liner 28 and a lower liner 30, which may be made of paper. Individual bandages 22 are sealed along their longitudinal side edges of upper and lower liner 28, 30, as well as at their ends 24. A lower layer 32 faces the adhesive portion of the bandage, and is treated with an anti-stick or release coating such as silicone. As an alternative, each bandage may have underneath its sticky ends a liner portion, to prevent adhesion to the lower layer 32. A gap region 34 on each side of the perforations 26 is made to be adhesive free, in order to allow the upper and lower bandage liners 28, 30 to be easily separated from the remainder of the roll at perforations 26, once the mechanism is actuated.

FIG. 3 discloses a cut away radial cross-section of the dispenser 10, showing one embodiment of the feeding drive and guide mechanism for the bandage dispenser. A plurality of drive and guide rollers 302, 304, 308, 310 are journaled in the housing of the dispenser 10 by shafts running through the rollers and held by the housing. A pinion drive roller 302 is driven as part of a rack and pinion arrangement. Drive roller 302 in turn drives upper pinch roller 304 in countervailing direction (as indicated by the reference arrows of rotation). Driver roller 304 cooperates with a lower pinch roller 308. Pinch rollers 304, 308 draw the leading edge 315 of bandage material from the roll of bandages 15. A lower guide roller 310 cooperates with the lower pinch roller 308 to draw away, guide and help remove one portion of the bandage liner, the bottom cover waste liner 314. The second portion of the bandage liner, the top portion 316, is stripped and ejected by cooperating rollers 302, 304, from the top of the dispenser to the rear, from an opening at the rear of the dispenser. An optional shroud 307 guards the bandage roll liner waste from entanglement with moving parts.

Drive roller 302 is engaged to be driven by a spring biased thumb knob 31, attached to a toothed rack 306 through a slot 19 extending along the radial cross-section of the dispenser frame, along with a return spring 352 biasing the knob to the retracted position. The rack 306 engages a pinion drive roller wheel 302, which may be a combination toothed and smooth roller, such as the roller 402 shown in FIG. 5. Pinion drive roller 302 is journaled to a portion of the frame that holds the pinion shaft running through the roller. Each of the other rollers also have journals in the dispenser housing to hold their respective shafts. Engaging the knob or thumb activator 31 with one's thumb (as shown in FIG. 1) and pushing with the thumb, against the knob return tension spring 352, moves the rack 306 across the pinion from an engaging position at distal point 350 to a position closer to a proximal point on rack 306 near the thumbswitch 31. The rack, thus translated, rotates the engaging pinion 302, which drives the drive pinch roller 304, which, in turn, engages drive pinch roller 308, and guide roller 310, to dispense a bandage from the bandage dispenser. In between drive pinch rollers 304, 308 is threaded the serially connected bandage roll 15. In between rollers 308 and 310 is threaded bottom cover liner waste sheet 314, while in between rollers 302, 304 is threaded top cover liner waste sheet 316.

To operate the bandage dispenser to dispense bandages, first a roll of bandages is inserted into the dispenser by threading the leading edge 315 of the bandage roll 15 through the dispenser. The top and bottom waste liners 316, 314 can also be threaded through their respective cooperating pinch rollers. The dispenser can be composed of two halves, which come apart to expose the internal mechanism of the dispenser. The roll 15 may be wound on a core, spool, or hub, or otherwise wound in a coil. Alternatively, the dispenser may be sealed, for single use only, and come already loaded with a bandage roll.

Next the user inserts an index finger in hole 360, which forms part of the handle for the frame, in that a user can support the frame with one's finger through hole 360. The user's thumb pushes down on spring loaded knob 31, as shown in FIG. 1. The bandage roll leading edge will move in the direction 21. Top and bottom liners 28, 30 will peel off and expose the sticky leading edge 315 (see FIGS. 1–3) of each individual bandage. The leading edge of the individual bandage, now shorn of its lining, is applied to the point of application, and the dispenser is pulled away to complete the bandage application. The point of application may be pressed with a pressure plate 362, to provide pressure to the sticky portion of the bandage.

Figure 4:
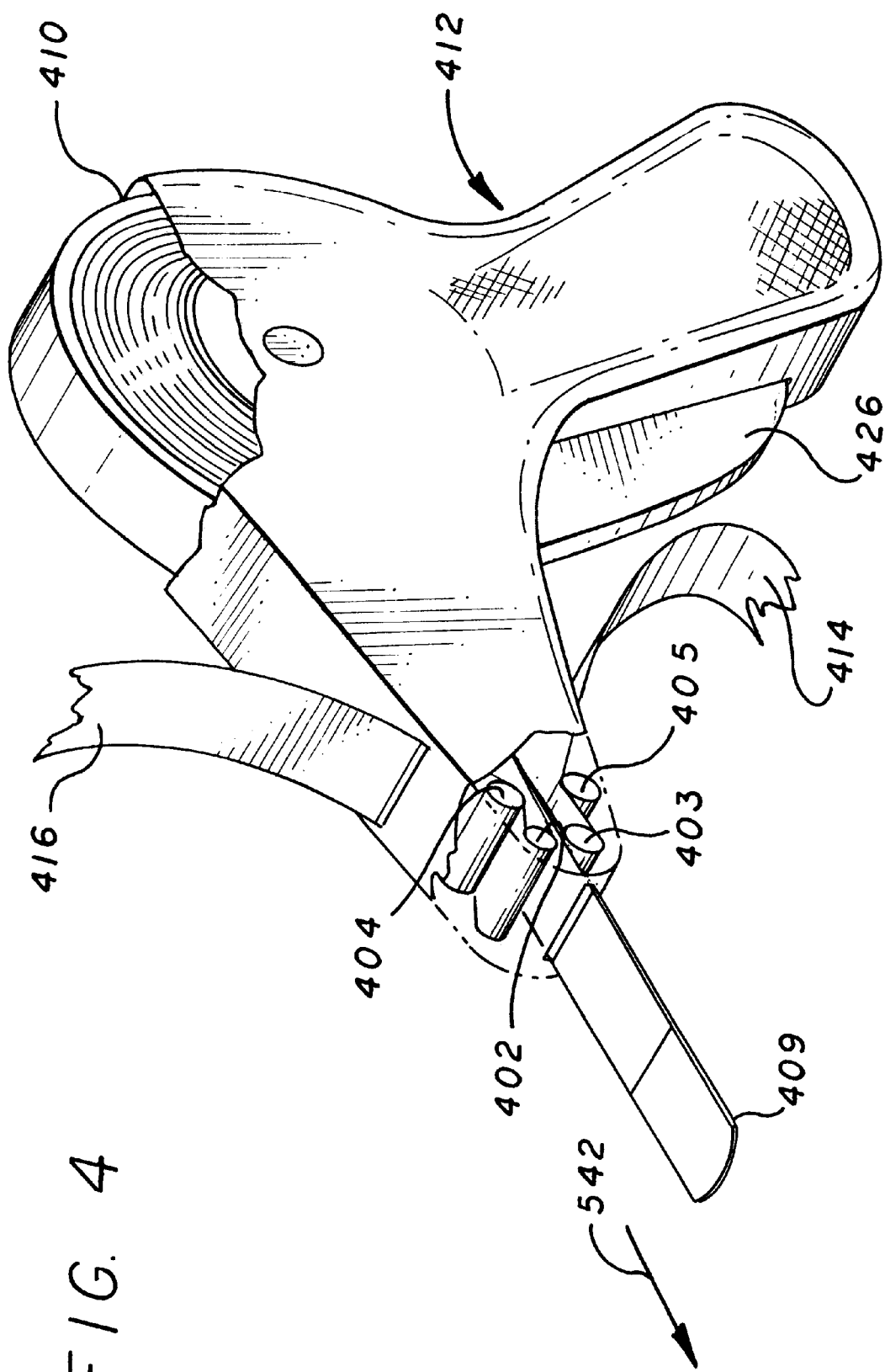
FIG. 4 is a partially cut away perspective view of another embodiment of the dispenser.
Figure 5:
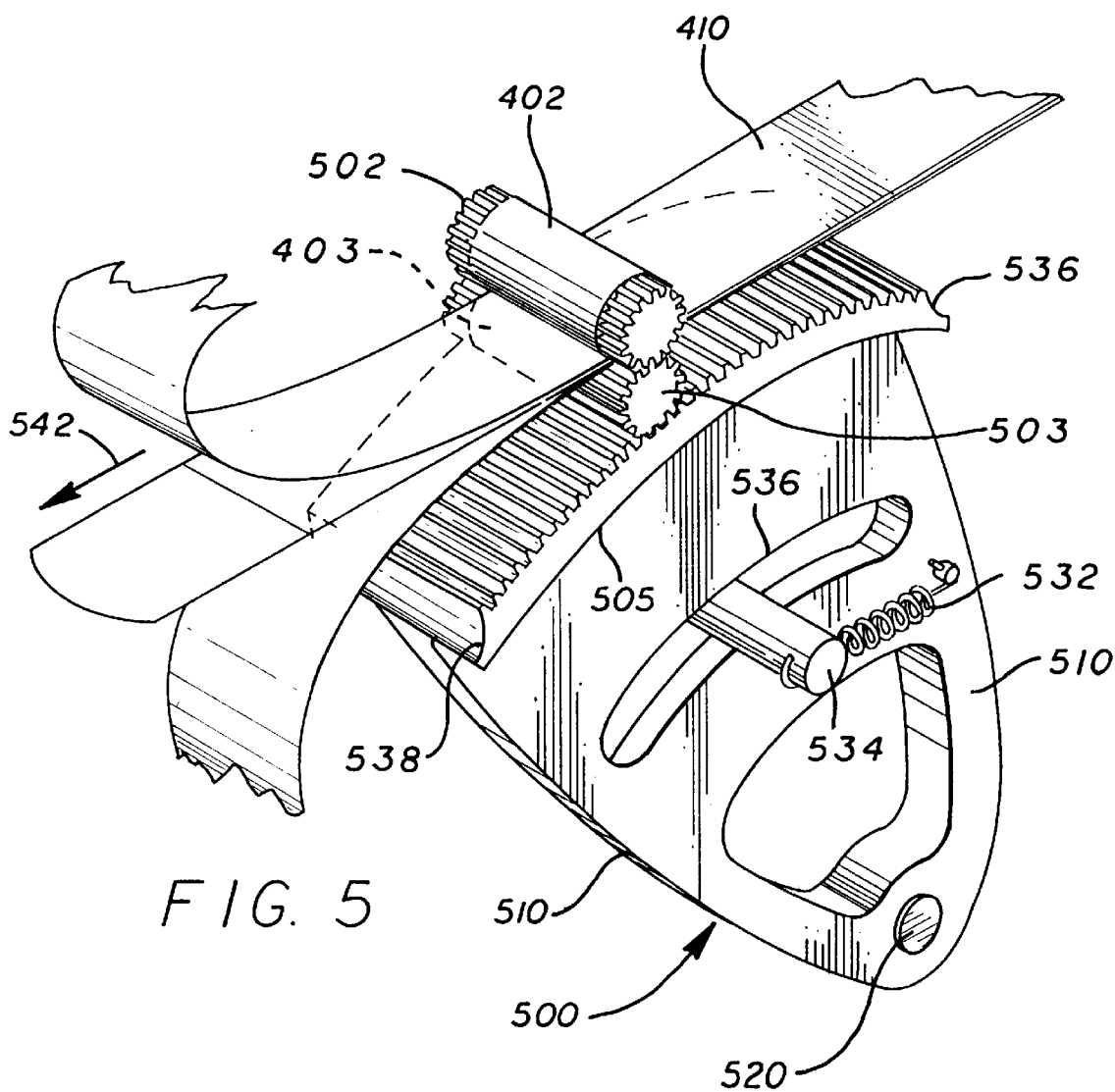
FIG. 5 is a view of the bandage feeding mechanism driving the driver rollers in the FIG. 4 dispenser.

FIG. 4 discloses another embodiment of the invention, employing a pistol grip. The FIG. 4 embodiment has a similar drive roller arrangement to the FIG. 3 embodiment described herein, comprising pinch drive rollers 402, 403, feeding the leading edge 409 of a roll 410 of serially attached, individually sealed bandages. A pistol grip frame 412 supports the rollers and roll. As best seen in FIG. 5, in lieu of a linear rack and pinion drive feeding mechanism, as in the FIG. 3 embodiment, the embodiment of FIG. 4 drives drive roller 403 by depressing the trigger 426, and through the rocker arm rack mechanism 500. A rack 505 engages driver roller 403 at pinion gear 503, which in turn is engaged with a second driver roller 402 at gear 502. The rack 505 resides on top of a rocker arm 510 which is pivoted about pivot point 520. The rocker arm rack 505 is biased by spring 532 to remain in a neutral position. The spring 532 may be a tension or compression spring, as appropriate. Another spring, in a mirror image reflection about fixed axis 534, may be disposed opposite spring 532 to maintain the rocker arm 510 in a neutral position. As can be seen, fixed axis 534, fixed to the housing, is attached to one end of the spring 532 to form a stable fixed anchor point for the spring while the other end of the spring is attached to rocker arm 510. A slot 536 allows the rocker arm 510 to pivot about pivot point 520 and swing past fixed axis 534. The spring 532, when thus elongated, opposes the rocker arm 510 whenever the rocker arm is pivoted past a neutral position of the rack mechanism 500. The spring(s) 532 provides a return force back to a neutral position by biasing the rocker arm 510 opposite the direction the rack mechanism 500 travels to when dispensing a bandage strip, which is when the mechanism 500 travels to the right (clockwise) in FIG. 5. Thus spring 532 provides a return force to restore the trigger 426 of the dispenser to a ready to fire position. Upon depressing the trigger 426, which can be operatively connected to, or one and the same with rocker arm 510, the rocker arm 510 and rack 505 rotate clockwise, engaging pinch drive rollers 402, 403 to rotate counter-clockwise to feed bandage strip leading edge 409 away from the dispenser, in the direction 542. Guide roller 405 cooperates with driven roller 403 to strip from the leading edge and lead away bottom bandage waste liner 414, while guide roller 404 cooperates with driven roller 402 to lead away top waste liner 416.

Regarding an idling or locking position of the FIG. 5 embodiment, there is shown an idling position 536, 538 (not to scale) on rack 505, which is a smooth portion on the rack 505 of the rocker arm 510. The idling position is for disengaging the rocker arm feeder drive mechanism 500 so that drive mechanism is in an idle position. Thus when the trigger is depressed furthest, the idling position 538 is reached, so the rack 505 does not engage pinion gear 503. A groove may be provided for the pinion to fall into and disengage from the rack when the idle position is reached. The trigger may be locked to remain in this idling position with a trigger lock, preventing further dispensing of bandages by the actuation of the trigger. Also, the roll of bandages may be more readily threaded through the rollers when the rack is in the idle position, as the pinion would free wheel. Other suitable disengagement and idling mechanisms may be employed from the teachings of the present invention.

Regarding both embodiments of the invention, the dispenser actuators (both the thumb knob actuator and the pistol grip trigger actuator) may be designed so that when fully depressed they dispense a single bandage, in order to promote uniformity in dispensing; in the alternative the dispenser actuators may dispense an integer multiple of bandages when fully actuated.

Further regarding the invention, from the teachings herein two dispenser units may be used in parallel fashion to dispense a plurality of different sized bandages. Thus, for example, two dispensers of the type shown in FIG. 4 are attached side by side, each of which may dispense bandages of a desired size depending on actuation of the selected trigger, or other actuator. In addition, suitable bandage feeding drive and guide mechanisms, other than the embodiments shown herein, can be employed from the teachings of the present invention. Moreover, the dispenser may be modified, using the teachings of the present invention, so that bandages from the bandage roll may be dispensed serially but with the outermost liner intact, which maintains the bandages in sterile condition. Thus the bandages would be dispensed still sealed inside their liners. The user would tear or cut individual bandages from the roll (along suitable tear lines) and the dispenser would thus dispense sterile bandages. For example, the dispensers described herein may be used in this embodiment, by simply not feeding the bandage upper and lower liners around the guide rollers when loading the bandage roll into the dispenser, so the liners are not stripped off and discarded at the back of the dispenser, but rather the liners are kept on the bandage roll and simply fed out with the bandage itself by the pinch drive rollers.

Although the present invention has been described in terms of the preferred embodiments above, numerous modifications and/or additions to the above-described preferred embodiments would be readily apparent to one skilled in the art. Thus, by way of example and not of limitation, frictional drive rollers may be employed instead of the rack and pinion mechanisms, and other known mechanical movements may be employed. It is intended that the scope of the present invention extends to all such modifications and/or additions and that the scope of the present invention is limited solely by the claims set forth below.

I claim:

1. A portable, hand-held bandage dispenser and bandage assembly comprising:
   a roll of serially wrapped bandages;
   a frame, a portion of the frame holding a roll of bandages supported by the frame and having a leading edge;
   a pair of pinch rollers supported by the frame, for engaging the leading edge of the roll of bandages, the roll of bandages having a plurality of individually wrapped bandages serially attached to one another at the ends of the bandages, wherein the serially wrapped bandages have an adhesive side;
   said serially wrapped bandages having a liner comprised of a top liner and a bottom liner, wherein the bottom liner is directly adjacent to the adhesive side of the serially wrapped bandages;
   a drive mechanism housed by the frame for driving the pinch rollers and dispensing bandages outside the frame;
   said dispenser including a plurality of guide rollers for separating and guiding the liner of said roll of bandages to expose the adhesive side of the serially wrapped bandages for direct application;
   said plurality of guide rollers including a first pair of rollers adjacent to one another to drive and guide said top liner, thereby ejecting said top liner from said dispenser housing, and said plurality of rollers including a second pair of rollers adjacent to one another to drive and guide said bottom liner, to eject said bottom liner from said dispenser housing, and;
   a handle for grasping the frame in a user's hand, wherein said dispenser is portable.

2. The invention according to claim 1, wherein:
   the drive mechanism comprises a rack and pinion;
   a thumbswitch connected to the rack, the rack translated by the thumbswitch to engage and rotate the pinion;
   a spring biasing the thumbswitch; and
   the pinion connected to the pinch rollers.

3. The invention according to claim 1, wherein:
   the drive mechanism comprises a rack and pinion;
   the rack forming part of a trigger for the dispenser;
   the rack pivoting about a pivot point;
   a spring biasing the rack to return to a neutral position when the rack pivots away from the neutral position;
   the rack pivoting away from the neutral position and rotating the pinion to drive the pinch rollers to dispense a bandage from the roll when the trigger is depressed;
   the handle for the frame being a pistol grip.

4. A bandage dispenser and bandage assembly comprising:
   a dispenser housing containing a roll of bandages therein, said roll of bandages having a plurality of serially attached bandages wrapped in a liner, said roll having a leading edge;
   said serially wrapped bandages having a top liner and a bottom liner;
   a feeding mechanism for engaging the leading edge of said roll of bandages to dispense said bandages from said dispenser housing;
   a plurality of guide rollers for separating and guiding the liner of said roll of bandages and ejecting the liner from said dispenser housing; and
   said plurality of rollers including a first pair of rollers adjacent to one another to drive and guide said top liner, thereby ejecting said top liner from said dispenser housing, and said plurality of rollers including a second pair of rollers cooperating to drive and guide said bottom liner, thereby ejecting said bottom liner from said dispenser housing.

5. The invention according to claim 4, wherein:
   said feeding mechanism comprises a pair of pinch rollers to drive said leading edge of said roll of bandages.

6. The invention according to claim 5, wherein:
   said feeding mechanism comprises a rack and pinion;
   a thumbswitch connected to said rack, said rack translated by said thumbswitch to engage and rotate said pinion;
   said pinch rollers operatively connected to said pinion.

7. The invention according to claim 6, further comprising:
   a spring biasing said thumbswitch, in a direction opposite the direction said thumbswitch travels when said feeding mechanism drives said leading edge of said roll to dispense a bandage from said roll.

8. The invention according to claim 5, wherein:
   said feeding mechanism comprises a rack and pinion;
   a trigger connected to said rack;
   said rack connected to pivot about a pivot point, said pinion connected to at least one of said pinch drive rollers;
   said rack rotating said pinion to drive said pinch rollers to dispense a bandage from said roll when said trigger is depressed.

9. The invention according to claim 8, further comprising:
   a spring biasing said trigger in a direction opposite the direction said trigger travels when said feeding mechanism drives said leading edge of said roll to dispense a bandage from said roll.

10. The invention according to claim 4:

wherein said feeding mechanism comprises a pair of pinch rollers;

further comprising a pair of guide rollers, said guide rollers cooperating with said pinch rollers to strip said liner from said roll of bandages.

11. The invention according to claim 10:

wherein said feeding mechanism comprises a gear driving said pinch rollers, and wherein said guide rollers are in contact with said pinch rollers to strip said liner from said leading edge of said roll of bandages.

12. The invention according to claim 11:

wherein said liner comprises a top liner and a bottom liner, said pair of guide rollers comprise two pairs of guide rollers, each pair of guide rollers cooperating with one of said pinch rollers to remove said top and bottom liners, respectively, from said leading edge.

13. The invention according to claim 4, further comprising:

a pressure plate disposed on the end of the dispenser frame, said pressure plate serving to provide pressure on bandages dispensed by said dispenser, and wherein said bandages are serially attached along their longitudinal ends.

14. The invention according to claim 4, wherein:

said drive mechanism has an idle position.

15. The invention according to claim 4, wherein:

said dispenser is made of plastic, is portable and sized to be grasped in an average adult hand.

16. A bandage dispenser and bandage assembly comprising:

means for storing a plurality of bandages;

means for dispensing said bandages serially from said dispenser;

said means for storing a plurality of bandages comprises a roll of bandages, said roll of bandages comprises a plurality of individually wrapped bandages, said bandages enclosed in two liners, a top liner and a bottom liner, said bandages connected to one another at their longitudinal ends, said ends scored with separation perforations to allow said bandages to be separated from said roll; and means for dispensing said bandages directly from said dispenser.

17. The bandage dispenser according to claim 16, wherein:

said bottom liner directly engages an adhesive layer on said bandages; and said means for dispensing said bandages directly from said dispenser includes a pair of guide rollers that mechanically separates said top liner and bottom liner so that said adhesive portion of bandage is exposed and ready for direct application.

18. A bandage dispenser and bandage assembly comprising:

a dispenser housing containing a roll of bandages therein, said roll of bandages having a plurality of serially attached bandages wrapped in a liner, said roll having a leading edge;

a feeding mechanism for engaging the leading edge of said roll of bandages to dispense said bandages from said dispenser housing;

said feeding mechanism comprising a pair of pinch rollers to drive said leading edge of said roll of bandages;

said feeding mechanism further comprising a rack and pinion;

a trigger connected to said rack;

said rack connected to pivot about a pivot point, said pinion connected to at least one of said pinch drive rollers; said rack rotating said pinion to drive said pinch rollers to dispense a bandage from said roll when said trigger is depressed; and said rack having a smooth portion for disengagement with said pinion, to idle said feeding mechanism.

\* \* \* \* \*